United States Patent [19]
Trapp

[11] Patent Number: 5,669,888
[45] Date of Patent: Sep. 23, 1997

[54] INJECTION NEEDLE PROTECTION DEVICE

[75] Inventor: Claude Trapp, Rueil Malmaison, France

[73] Assignee: Matef, France

[21] Appl. No.: 188,875

[22] Filed: Jan. 31, 1994

[51] Int. Cl.[6] .................................................. A61M 5/00
[52] U.S. Cl. .................................. 604/263; 604/171
[58] Field of Search ............................ 604/110, 198, 604/263, 192, 197, 171, 241–243, 283, 905

[56] References Cited

U.S. PATENT DOCUMENTS

| | | | |
|---|---|---|---|
| 4,631,057 | 12/1986 | Mitchell | 604/198 |
| 4,702,738 | 10/1987 | Spencer | 604/198 |
| 4,743,233 | 5/1988 | Schneider | 604/192 |
| 5,108,376 | 4/1992 | Bonaldo | 604/171 |
| 5,154,699 | 10/1992 | Ryan | 604/198 |
| 5,156,599 | 10/1992 | Ranford et al. | 604/198 |
| 5,219,339 | 6/1993 | Saito | 604/198 |
| 5,306,258 | 4/1994 | de la Fuente | 604/198 |
| 5,342,308 | 8/1994 | Boschetti | 604/198 |
| 5,344,405 | 9/1994 | Richards | 604/198 |
| 5,360,408 | 11/1994 | Vaillancourt | 604/198 |
| 5,401,250 | 3/1995 | Shields | 604/192 |
| 5,403,288 | 4/1995 | Stanners | 604/197 |

FOREIGN PATENT DOCUMENTS

| | | | |
|---|---|---|---|
| 2225723 | 6/1990 | United Kingdom | 604/192 |

*Primary Examiner*—Corrine M. McDermott
*Assistant Examiner*—Ronald K. Stright, Jr.
*Attorney, Agent, or Firm*—William A. Drucker

[57] ABSTRACT

A tubular guard 14 encircles the needle 6 and exhibits a conical connection surface which, in the protection position, cooperates with a conical connection surface of the joining piece bearing the needle 6. By pushing on the cap 16 covering the needle 6, the joining piece and the associated guard are secured to the handpiece 1. The collar 17 is then pressed onto the guard 14 and frees the guard from the joining piece. The guard 14 is then hooked onto the handpiece 1 by freeing the end of the needle 6.

3 Claims, 2 Drawing Sheets

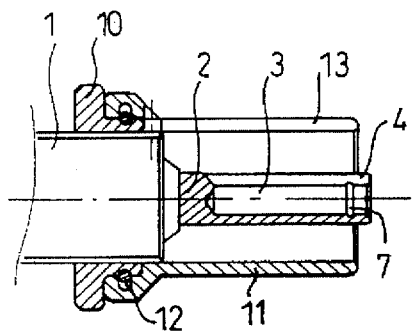
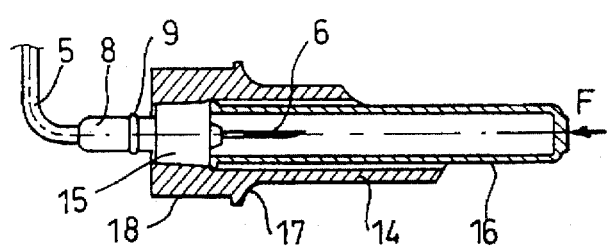
FIG.1a  FIG.1b
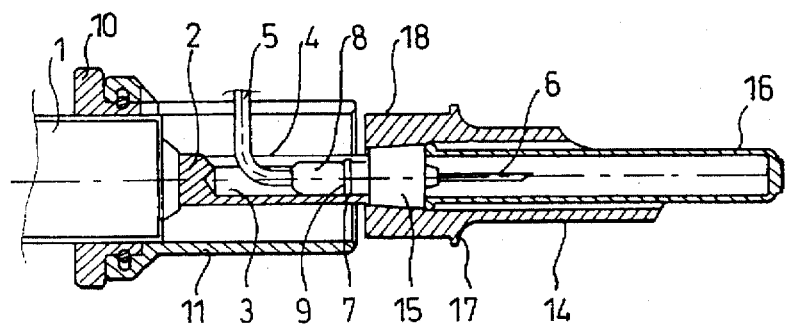
FIG.2
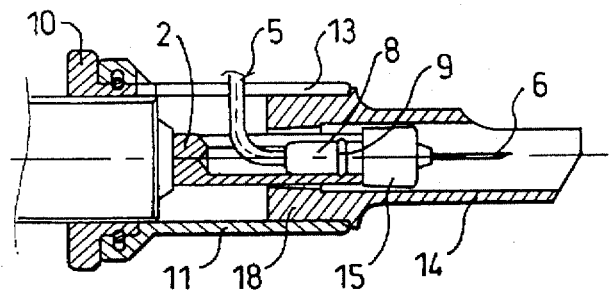
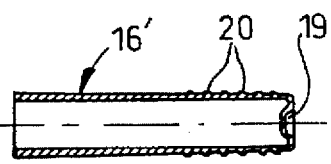
FIG.3  FIG.4
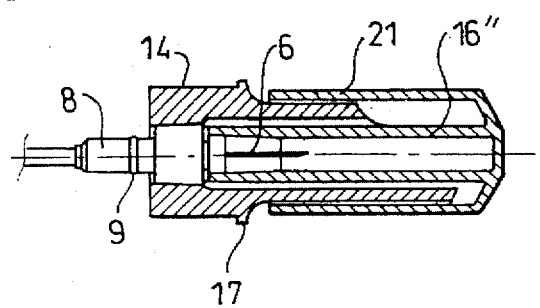
FIG.5

5,669,888

INJECTION NEEDLE PROTECTION DEVICE

FIELD OF THE INVENTION

The invention concerns injection devices used mainly for medical, but also veterinary and food usages.

Such devices are known in the field of medical appliances. Thus, the U.S. Pat. No. 3,880,163 describes a handpiece containing a piston syringe equipped with an injection needle and two springs, one for pushing a catapult bearing the syringe for mechanically introducing the needle into the flesh of the patient to be treated, the other borne by the catapult for pushing the piston into the syringe and inject the treatment liquid through the needle.

This needle is protected prior to use by a movable cap and in addition is surrounded by a tubular dismantable adustable guard engaged on the end of the handpiece and able to touch the skin of the patient.

The use of these various elements and in particular their placing and removal from the handpiece requires a large number of movements and considerable attention on the part of the practician so as to avoid him pricking himself.

In addition, it has recently appeared that all the elements able to possibly touch the patient are disposable so as to avoid contaminating another person.

The invention satifies this requirement and in addition needs the practician to carry out simple safe handlings of the various elements. It preferably, but not necessarily, is applicable to the medical device comprising a handpiece with an injection catapult described in the French patent application No 92.03870 filed on 31 Mar. 1992.

The document EP-A-0 485 345 describes a syringe for single usage comprising a needle protection guard. This guard is engaged on the syringe and is able to slide between a safety position in which connection surfaces it bears engage additional connection surfaces borne by the support joining piece of the needle, and a use position where its connection surfaces engage other connection surfaces borne by the syringe.

The document FR-A-978 344 describes a device activating an injection needle via the resilience of a spring. This device comprises around the needle a fixed guard having an oblique groove.

According to the invention, the protection device for an injection needle having a joining piece adapted to a catapult sliding in a support guide of an injection device comprises a guard which encircles the needle and which may be engaged on a piece held longitudinally on the support guide, mutual connection surfaces of firstly the joining piece and secondly of the guard able to be disconnected from one another when engaging the guard on said piece so as to leave free the penetration movement of the needle independently of the guard after it has been engaged, and is characterized in that said connection surfaces comprise cooperating portions slanted relatively to the axis of the needle so as to drive the latter when the guard is extracted from its engaging with said piece.

The device further preferably comprises a pushing piece inside the guard and is able to firstly push the joining piece of the needle against the catapult so as to make it secure on the latter and secondly be placed out of action so as to leave free the movement of the needle inside the guard.

Said pushing piece may consist of a cap pressing on the fixing joining piece of the needle and which is withdrawn before or after engaging the guard on the end of the handpiece.

BRIEF DESCRIPTION OF THE DRAWINGS

So as to clearly understand the device of the invention, there now follows non-restrictive examples of several embodiments with reference to the accompanying drawing on which:

FIG. 1a is a partial diametral sectional view of the end of an injection device;

FIG. 1b, shown opposite FIG. 1a, is a partial diametral sectional view of a first embodiment of a protection device according to the invention;

FIG. 2 is a partial diametral sectional view showing the fixing of the device of FIG. 1b on the end of the catapult of the injection device;

FIG. 3 is a view corresponding to FIG. 2 and shows the same pieces in the injection position;

FIG. 4 is a diametral sectional view of a variant of the pushing cap;

FIG. 5 is a diametral sectional view of another variant of a cap mounted with a protection device according to the invention;

DETAILED DESCRIPTION OF THE PREFERRED EMBODIMENTS

Figures 6, 7, 8:
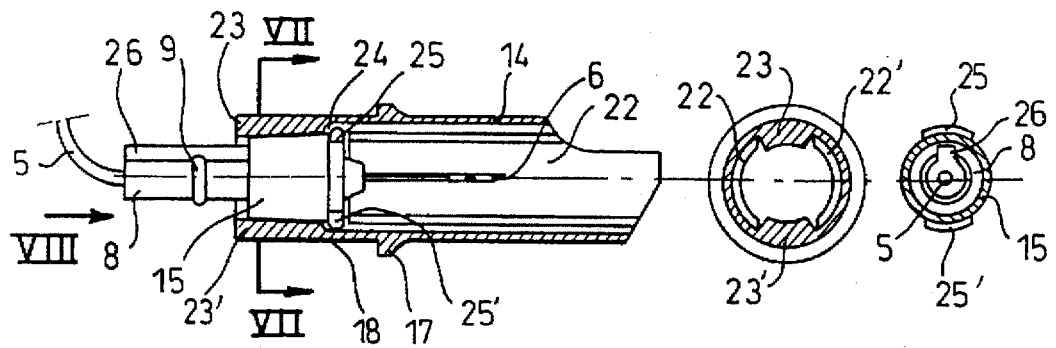
FIG. 6 is a partial diametral sectional view of a second embodiment of the protection device of the invention.
FIG. 7 is a transverse vertical section taken along the line VII—VII of FIG. 6.
FIG. 8 is a view of the fixing joining piece along the arrow VIII of FIG. 6.

The injection device comprises, as regards all the embodiments described and as indicated on FIG. 1a, a cylindrical guide support 1 inside which a catapult can slide and whose end 2 comprises a bore 3 provided with a radial slit 4 enabling a flexible feed tube 5 of the injection needle 6 to pass through which are shown on FIG. 1b.

In addition, a circular groove 7 of this bore enables, by means of the elasticity of the bore 3, to support the fixing joining piece which comprises a cylindrical portion 8 with a diameter adapted to the bore 3 and a circular flange 9 able to penetrate into the groove 7.

The portion of the injection device (not shown on the drawing) is for example of the type described in the above-mentioned French patent application No 92.03870.

Around the guide 1, threaded externally, is a bolt 10 which longitudinally retains an engaging piece 11 by means of a broken elastic ring 12. The engaging piece 11 exhibits a radial slit 13 able to allow the flexible tube 5 to pass and which can be orientated inside the plane of the slit 4 by rotating the piece 11 around the ring 12. By rotating the bolt 10, it is possible to adjust the longitudinal position of the piece 11, thus also adjusting the penetration depth of the needle 6, as shall be seen subsequently.

According to the first embodiment shown on FIG. 1b, the device of the invention comprises a guard 14 connecting with the fixing joining piece of the needle 6, this connection resulting from introducing a male cone 15 of the joining piece into a female cone of the guard 14.

The guard 14 is formed by a tube whose bore coaxially encircles the needle 6 and is obliquely scalloped opposite the end of the latter. This scalloping enables the practitioner to aim the injection point at the center of the arc of a circle of the end placed in contact with the skin of the patient.

The bore of the guard 14 with slight rubbing receives a cap 16. The open end of this cap comes to rest on the large-diameter face of the cone 15.

By pushing on the cap along the arrow F of FIG. 1b and after having made the tube 5 pass into the slits 4 and 13, the cylinder 8 of the joining piece can be pushed into the bore 3 until the flange 9 is clipped into the groove 7. FIG. 2 shows the position of various elements at the moment when the needle 6 is fixed to the catapult.

Fixing may also be embodied by radially pushing the cylinder 8 onto the end 2 through the slit 4. In this case, the cap 16 is not used as a pushing piece.

Then, in order to free the needle from its guard 14, the latter is then pushed by its collar 17 so as to introduce, as shown on FIG. 3, the cylindrical portion 18 of the guard 14 into the engaging piece 11, this engaging being carried out by gentle rubbing. The end of the needle 6 is then close to the guard 14 and this is because the nut is more engaged by screwing onto the guide 1. At the same time of this engaging, the cone 15 leaves the female cone of the guard 14, thus disconnecting the latter from the needle 6.

The removal of the cap, as shown on FIG. 3, then makes it possible to carry out injection or successive injections whose depth is determined by the movement of the catapult and by a slight pressing of the guard 14 around the injection point.

After the injection has been carried out, the cap 16 may, if required, be replaced. The guard 14 is then pulled up so as to remove it from the engaging piece 11 and render it again integral with the needle via the cone 15 of its joining piece returning to the position of FIG. 2. A firmer traction using in particular the collar 17 then pulls out the joining piece with the catapult, this strongly accentuating the engagement of the cone 15 in the guard and thus avoiding any separation which would lay bare the needle 6. The flexible tube may then be safely dismounted and disposed of the injection unit possibly infected by the actual injection.

The cap 16' shown as a variant on FIG. 4 and specially adapted for the usage of the pushing piece according to the invention, comprises a slight depression 19 at its closed end so as to avoid any skidding of the finger of the practician at the time of pushing, as well as causing any lateral marks 20. These details in addition remind the practician of the specific use of this cap as a pushing piece for fixing the needle 6 on the injection device.

The cap 16" shown as another variant on FIG. 5 further comprises a sheath 21 which surrounds, at least partially, the guard 14 which virtually obliges the practitioner to firstly use it as the pushing piece without acting on the guard 14 before fixing it on the catapult.

In the embodiment of FIGS. 6, 7 and 8, there now follows a description of the elements having the same function as in the preceding embodiment bearing the same reference numbers.

The device then includes two pushing pieces 22, 22' of limited width and relief fixed or moulded symmetrically inside the bore of the guard 14. The female cone of this guard is reduced to two portions 23, 23' in the extension of the bore portions without any pushing pieces. This facilitates moulding of the guard in a single operation whilst leaving a fully circular cavity 24 between the cone portions and the pushing pieces.

The fixing joining piece comprises two radial stops 25, 25' of small width and able to be introduced between the pushing pieces 22, 22' as far as into the cavity 24, a position in which this joining piece may by means of its cone be connected to the cone portions 23, 23'.

From this connection position, the cylinder 8 may be disposed in the bore of the capacity, be pushed by the guard 14 to free the conical surfaces from one another, have the pushing pieces 22, 22' by possibly rotating the guard 14 disposed opposite the radial stops 25, 25' and forcefully push the guard to ensure that it is fixed to the catapult by means of the flange 9.

Then via a rotation of one quarter, the stops 25, 25' opposite are suppressed from the thrust members pieces 22, 22', which enables them to pass between the latter when the cylinder 18 is engaged in the end of the handpiece when the catapult is then activated.

It is to be noted that a longitudinal protruberance 26 of the cylinder 8 cooperates with the groove 4 of the catapult by penetrating into the latter, which prevents the joining piece from rotating during the rotations carried by the practitioner with the guard 14.

Figure 9:
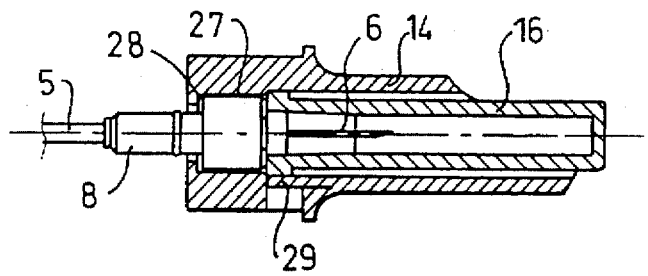
FIG. 9 is a partial diametral sectional view of a third embodiment of the device of the invention.
Figure 10:
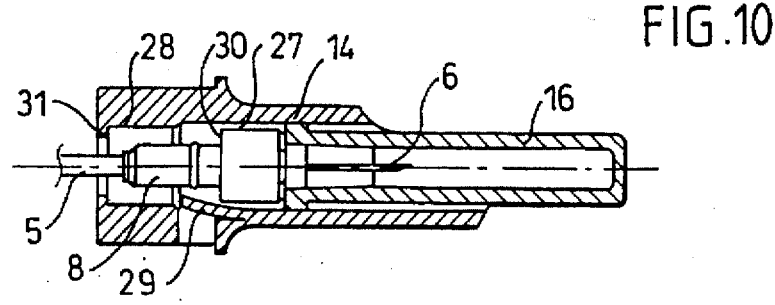
FIG. 10 is a view corresponding to FIG. 9, but with the pieces in the injection position.
Figure 11:
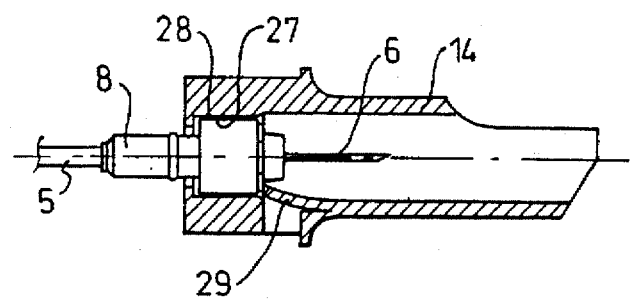
FIG. 11 is a view corresponding to FIGS. 9 and 10 showing the same pieces locked together and without the cap.

A third embodiment is represented on FIGS. 9, 10 and 11.

In this case, the connection surfaces 27, 28 are cylindrical, which is much easier to embody than conical surfaces. In addition, the manufacturing tolerances are wide since said surfaces do not in this instance have to provide tightening so as to retain the joining piece in the guard 14. In fact, this retention is thus carried out by means of a catch 29 joined to the periphery of the guard 14 with an elastic effect so that it tends to penetrate inside the bore of the guard.

Initially, the cap 16 keeps the catch spaced apart, and, in its pushing movement during the engaging of the guard 14, the catch passes around the connection surface 27 of the joining piece, as shown on FIG. 10. At the end of the operation, following withdrawing of the cap 16, the traction of the guard connects the cylinder 27 with the cylinder 28 until a shoulder 30 of the joining piece abuts against a shoulder 31 of the guard 14 which makes it possible to free the joining piece from the catapult.

At the same time, the catch 29 draws closer to the needle and stops the latter from sliding into the guard by abuting on the joining piece of the needle 6, as shown on FIG. 11.

One use variant of this third embodiment consists in firstly removing the cap 16 to free the catch 29. The joining piece 8 may thereupon be fixed to the catapult by pushing the guard 14 whose catch 29 presses on the joining piece of the needle 6, thus constituting the pushing piece of the invention.

Then a slight pressure on the cap 16 moves away the catch 29 and a new pushing on the guard 14 enables it to be engaged in the piece 11 of FIG. 1a.

At the end of the operation, the catch 29 plays the same retention role as previously.

It can be readily understood that the above description has been given solely by way of non-restrictive example and constructive modifications or additions could be made to it without departing from the context of the invention.

What is claimed is:

1. An injection apparatus with injection needle protection device, comprising:

(a) an injection needle carried by a joining piece, (b) a cylindrical guide support with a member extending therefrom, said member presenting a bore receiving said joining piece, (c) an engaging piece rigid with said guide support and surrounding said member, (d) a guard along said joining piece having two positions, a protection position surrounding said injection needle and a second position in which said guard engages a bore provided axially between the member and a peripheral wall of said engaging piece exposing said needle, (e) a pushing piece bearing on said joining piece and disposed around said injection needle and within said guard, said pushing piece when actuated pushing said joining piece into said bore of said member and said guard to its second position into the bore of said engaging piece, (f) connection surfaces provided on said joining piece and slanted with relation to the axis of said joining piece and complementary connection surfaces provided on said guard and slanted with relation to the guard axis, said connection surfaces mutually engaging when said guard is moved from its second position to its protection position thus ensuring separation of said joining piece from said member.

2. Device according to claim 1 wherein said pushing piece consists of a protuberance extending into a bore of the guard, said protuberance in a position allowing to push said joining piece on a stop provided on said joining piece.

3. Device according to claim 2 wherein said protuberance and said stop each have a reduced width, said guard being rotatable with relation to said joining piece to draw said protuberance out of its position facing said stop.

* * * * *